United States Patent [19]

Ruiz

[11] Patent Number: 5,569,467
[45] Date of Patent: Oct. 29, 1996

[54] PROCESS FOR THE PREPARATION OF MICROBALLS AND MICROBALLS THUS OBTAINED

[75] Inventor: Jean-Marc Ruiz, Vernouillet, France

[73] Assignee: Societe de Conseils de Recherches et d'Applications (S.C.R.A.S.), France

[21] Appl. No.: 243,571

[22] Filed: May 16, 1994

Related U.S. Application Data

[63] Continuation-in-part of Ser. No. 67,354, May 24, 1993, abandoned.

[30] Foreign Application Priority Data

May 15, 1993 [GB] United Kingdom .................... 9310030

[51] Int. Cl.⁶ ..................................................... A61K 9/14
[52] U.S. Cl. ............................................ 424/489; 424/501
[58] Field of Search ....................................... 424/489, 501

[56] References Cited

U.S. PATENT DOCUMENTS

| | | | |
|---|---|---|---|
| 4,010,125 | 3/1977 | Schally et al. | 260/8 |
| 4,675,189 | 6/1987 | Kent et al. | 424/490 |
| 4,767,628 | 8/1988 | Hutchinson | 424/426 |
| 4,844,910 | 7/1989 | Leslie et al. | 424/494 |
| 4,867,985 | 9/1989 | Heafield et al. | 424/461 |
| 5,019,400 | 5/1991 | Gombotz et al. | 424/497 |
| 5,213,812 | 5/1993 | Ruiz | 424/499 |
| 5,225,205 | 7/1993 | Orsolini | 424/489 |

FOREIGN PATENT DOCUMENTS

| | | |
|---|---|---|
| 0058481 | 10/1986 | European Pat. Off. . |
| 9221326 | 12/1992 | WIPO . |

OTHER PUBLICATIONS

E. Mathiowitz et al., "Polyanhydride Microspheres as Drug Carriers: Hot–Melt Microencapsulation", Journal of Controlled Release, 5;1 (1987) 13–22.

*Primary Examiner*—James J. Seidleck
*Assistant Examiner*—John M. Cooney, Jr.
*Attorney, Agent, or Firm*—Lucas & Just

[57] ABSTRACT

A method of making microballs is disclosed. An active ingredient, a biocompatible polymer and a supporting phase, such as silicone oil, are stirred at a temperature above the Tg of the polymer and below the temperature at which any of the ingredients vaporizes or degrades. Stirring is continued until microballs of the desired diameter are formed, whereafter the mixture is cooled and the microballs are separated from the supporting phase. The microballs are substantially spherical, substantially smooth on their external surface and have substantially no active ingredient on their external surface.

43 Claims, No Drawings

PROCESS FOR THE PREPARATION OF MICROBALLS AND MICROBALLS THUS OBTAINED

This is a continuation-in-part of application Ser. No. 067,354 filed May 24, 1993 now abandoned.

The present invention relates to microparticles and, in particular, to a process for preparing microballs which does not require any solvent or mechanical treatment of the active ingredient. It also relates to the microballs thus obtained, which are characterized by being substantially spherical and substantially free of active ingredient on the external surface.

Microparticles are small pharmaceutical particles comprising a biocompatible polymer and an active ingredient. Microparticles are used, for example, as sustained release compositions, i.e. the polymer slowly biodegrades or is resorbed by the body, and as the polymer biodegrades or resorbs, the active ingredient is released.

One of the problems with microparticles is the "burst effect". The burst effect is the phenomenon which occurs when microparticles are first consumed or injected into the human or animal being treated. Upon injection, all of the material on the surface of the microparticle can be immediately consumed by the body. This means that the body gets an excessively large dosage at initial injection. It is advantageous both to control the burst effect and to make sure that, throughout the life of the microparticles, the dosage available to the body is above the minimum level at which they are efficient.

It has been found that forming the microparticles so that they are substantially free of active ingredient on the surface of the microparticles makes better control of the burst effect. One of the advantages of microparticles with substantially no active ingredient on the surface is that they have a more easily controlled release profile.

It is to be understood that when it is said that the microparticles have essentially no active ingredient on the surface, it is intended to mean that the microparticles are uncoated, i.e. they do not have a separate coating on the external surface thereof. The microparticles are substantially free of active ingredient at the surface because of the manner in which they are formed, not because they have an external coating.

One way to accomplish this is discussed in my prior U.S. Pat. No. 5,213,812 issued May 25, 1993. As set forth in that patent, microparticles are prepared with substantially no active ingredient on the surface by a process which includes extrusion, tabletting, grinding or other mechanical treatment of the particles to be made into microparticles.

While the process of my U.S. Pat. No. 5,213,812 is a vast improvement over previous processes for making microparticles, it has been found that there are further improvements which can be made. One of the disadvantages of the mechanical treatment is that it creates irregularly shaped particles which do not give uniform release of active ingredient, and which can have uncontrollable burst effect. Another disadvantage is that some active ingredients are fragile and are damaged or destroyed by the mechanical steps of grinding, tabletting, extrusion, etc. Furthermore, up to 5% of the active ingredient can be lost during the mechanical processing. This is significant for two reasons. One is the high cost of many pharmaceutical materials, notably peptides, where the loss of up to 5% active ingredient can be significant. Furthermore, since the exact amount of material lost is not ascertainable, the amount of active ingredient administered cannot be accurately controlled.

Some processes for producing particles without the need for extruding and/or grinding techniques are known. For example, PCT Application WO92/21326 discloses a process of forming microparticles from a mixture of drug and biocompatible polymers by heating the combination to an intermediate liquid phase and then pouring the liquid phase on a temporary matrix consisting of crystals. The liquid phase is converted to a solid phase by cooling and then the matrix is removed from the solid phase by washing. The solid phase is thus in a form comprising imprints of the structure of the temporary matrix crystals. Consequently, the particles obtained are similar to those obtained by mechanical treatment in that they have an irregular external surface and are non-spheroidal, and do not provide the characteristics required for an accurate control of the release.

Another process, called hot-melt encapsulation, is described in E. Mathiowitz and R. Langer, Journal of Controlled Release, 5 (1987), 13–22. The process comprises the mixture of a drug and a melted polymer. The mixture is the suspended solvent which is immiscible with the selected polymer and drug. An emulsion is obtained, stabilized and then cooled until solidification of the core material. The drawback to this process is that the polymer used has a low melting point, e.g. 70°–80° C. or lower. If it is desired to use a polymer with a higher melting point, the polymer must be combined with a plasticizer in order to lower the melting point down to a temperature at which the process may be performed. This is because the use of a high processing temperature, which would be necessary to use the process with a pure polymer having a high melting point, leads to both sticking of the ingredients and degradation of the drug. Thus, it is impossible to obtain particles comprising only the drug and a high melting point polymer. Furthermore, the microparticles obtained have a granulated external surface and the disadvantages as previously discussed.

According to the invention there is disclosed a new process for the preparation of microballs wherein the drawbacks which exist in the techniques described in the previous processes are avoided.

In comparison with the process of the above cited U.S. '812 patent, the process of the present invention is performed without using mechanical formation of the particles. In accordance with the present invention, the starting materials may be limited to the constituents of the microballs and a supporting phase. The processing techniques can be limited to heating, cooling and stirring; conventional techniques, such as dry mixture, extrusion and grinding, are not necessary. Furthermore, the particles of the present invention are dry processed without use of any solvents.

The microparticles obtained according to the present invention are also of substantially spheroidal form and have substantially no active ingredient on the external covering. The process of the invention may be used to obtain microballs with a core loading of 1%, 5%, 10%, 15% or above.

The present invention improves on the formation of microparticles by forming microballs, i.e. substantially spherical microparticles, which have substantially no active ingredient on the surface thereof by eliminating the need for mechanical treatment of the ingredients making up the microballs. In accordance with the present invention, a supporting phase is used for the formation of the microballs. The supporting phase is immiscible with the active ingredient and the polymer of the microballs to be formed. The supporting phase preferably has a viscosity of from about 3,000 to about 15,000 mPa.s at 25° C.

The supporting phase is heated to a temperature above the glass transition temperature (Tg) of the polymer and below the decomposition temperature of the active ingredient or the polymer, whichever is lower. It will be appreciated that if the Tg of a particular polymer is above the decomposition temperature of the active ingredient to be used, then that particular polymer cannot be used to make microballs with that particular active ingredient.

The active ingredient and the polymer can be added to the supporting phase together or they can be added separately. Furthermore, each may be added to the supporting phase before it is heated, while it is being heated, or after it has reached the desired temperature. Still further, the active ingredient and the polymer can be pre-mixed before being added to the supporting phase.

After the supporting phase, polymer and active ingredient are at the selected temperature, they are stirred and the stirring is continued for a time and at a shear rate effective to form microballs of the desired size. The amount and rate of stirring must be empirically determined for each combination of polymer and active ingredient. Furthermore, since the microballs can be made of different sizes depending on the amount of stirring, the desired size of the particles will also affect the empirical determination of the amount of stirring required.

While the ingredients may be combined in any selected order, it is preferred that the polymer first be incorporated into the supporting phase and that the supporting phase be stirred until microballs of polymer of the desired size are obtained. Then, while continuing the stirring at the temperature above the Tg of the polymer, the active ingredient is added. The active ingredient may be added in either solid or liquid form. Stirring is continued during the addition of the active ingredient until complete absorption of the active ingredient by the polymer. Complete absorption must be empirically determined for each combination of polymer and active ingredient. This particular variation of the process is especially desirable where the active ingredient has a comparatively low degree of thermostability. The reason this variation of the process is desirable is because the active ingredient is at an elevated temperature for a relatively short period of time.

Where the active ingredient is stable at high temperatures, e.g. between 100° C. and 200° C., the active ingredient can first be added to the supporting phase. The supporting phase and active ingredient can then be heated above the Tg of the polymer to be added, whereafter the polymer is added and the mixture is stirred until microballs of the desired size are obtained.

After the microballs are formed to the required size, the stirring is discontinued and the mixture is cooled. An appropriate washing agent, which is a solvent for neither the polymer nor the active ingredient, is used to wash the microballs and then the microballs are recovered by filtration and drying.

After filtration, the microballs can be subjected to a sterilization step. However, if the selected temperature to which the mixture of the supporting phase, the microparticles and the polymer is high enough, this step can act as the sterilization step rather than requiring a separate sterilization step. It is also within the contemplation of the present invention to sterilize the active ingredient before it is added to the supporting phase, thus eliminating the need for a separate sterilization step or using a temperature during the processing which is high enough to act as a sterilization step. In any case, the microballs obtained according to the process of the invention may be sterilized if desired. Any known technique can be used such as, for instance, radiosterilization.

The essential characteristics of the supporting phase are that it be immiscible with the selected polymer and the active ingredient and that it have a boiling point which is above the temperature which is selected to form the microballs. The supporting phase may be a homopolymer or a copolymer or a combination of two or more of the same. Suitable for use as a supporting phase are liquids such as silicone oil, sesame oil, peanut oil, castor oil and the like. Appropriate thickening agents, such as stearates, may be added to the supporting phase if desired. The viscosity of the supporting phase is suitably from about 3,000 to about 15,000 mPa.s (at 25° C.). Preferably, the viscosity is of from about 5,000 to about 12,000 mPa.s (at 25° C.) and, more preferably, about 10,000 mPa.s (at 25° C.).

The supporting phase may suitably be a hydrophobic or hydrophilic gel. When the gel is hydrophobic, the active ingredient is preferably hydrophilic. With a hydrophobic supporting phase, the microballs may suitably be recovered by washing the mixture with a hydrophobic washing agent, e.g. myristic acid isopropyl ester. When the supporting phase is hydrophilic, the active ingredient is preferably hydrophobic; these microballs may suitably be recovered by washing the mixture with a hydrophilic washing agent, e.g. water or a mixture of water and ethanol. Silicon oil is the preferred supporting phase in many instances. The reason is that the hydrophobic or hydrophilic nature of the active ingredient is usually not an issue because of the insolubility of most active ingredients in silicon oil.

Suitable polymers and active ingredients are well known in the art and are set forth, for example, in my prior U.S. Pat. No. 5,213,812, the relevant teachings of which are incorporated herein by reference.

Suitable polymers include polyanhydrides, polyacetals, polysaccharides, cellulosic polymers (e.g. hydroxymethyl cellulose, hydroxypropylmethyl cellulose), polyvinylpyrrolidone and polypeptides. The polymer must be biocompatible and may also be biodegradable or bioresorbable. Suitable biodegradable polymers include homopolymers and copolymers of ε-caprolactone, denatured proteins, polyortho esters and polyalkyl-cyanoacrylates. Suitable bioresorbable polymers include homopolymers and copolymers of lactic acid and glycolic acid. It will be understood that other polymers can be used and that the polymer used may be a homopolymer of any one of the foregoing or of any suitable polymer, or a copolymer of any two or more of the foregoing or of any two or more other suitable polymers. It is preferred that the selected polymer have a Tg between about 25° C. and about 200° C. and, even more preferably, the selected polymer has a Tg between about 35° C. and about 150° C. In addition to the importance of the Tg, the melting point of the polymer is also important. The melting point should be high enough so that the microballs do not melt and stick together under normal use conditions. It is preferred that the melting point of the polymer be at least about 75° C., more preferred that it be at least about 100° C., and most preferred that it be above about 150° C.

The term "active ingredient" is broad and includes any pharmaceutically active ingredient or a mixture of two or more pharmaceutically active ingredients. The active ingredient may be in either liquid or solid form. Pharmaceutically active ingredients are those which can be administered to humans or animals for the purpose of diagnosis, cure, mitigation, treatment or prevention of disease. Typical active ingredients which can be used in microballs include narcotics, such as morphine; narcotic antagonists, such as naloxone; antipsychotic agents, such as sodium pentobarbital and chlorpromazine; antidepressives, such as imipramine hydrochloride; stimulants, such as methyl phenadate and nikethamide; hallucinogens; analgesics, such as mumorphan meperidine; anorexigenic agents; antihypertensive agents, such as reserpine; antianginal agents, such as papaverine; drugs for the therapy of pulmonary disorders, such as theophylline ethylene diamine salt; chemotherapeutic agents; antiparasitic agents, such as emetine hydrochloride; antifungal agents, such as cyclohexemide; anti-neoplastic agents, such as triethylene thiophosphoramide; agents affecting metabolic diseases and endocrine functions, such as prostaglandins; athersclerosins, such as heparin; steroids and biologically related compounds; polypeptides, such as bacitracin and polymyxin B sulfate; natural and synthetic hormones, such as progesterone; steroid and non-steroidal anti-inflammatory agents, such as hydrocortisone; agents affecting thrombosis, such as crystalline trypsin; vitamins, such as vitamin B12; anti-epilepsy agents, such as phenobarbital, and the like. It should be understood that the specific drugs mentioned by name are illustrative and not limitative.

In addition to the active ingredient in the microballs, there can be included pharmaceutically inert additives such as PvP, mannitol, carbowax, polyethylene glycols, glycerides and ethyl cellulose. The term "active ingredient" also includes the lack of presence of an active ingredient. This can be used, for example, where it is desired to have some of the subjects treated with an active ingredient and other of the subjects treated with a placebo. In this case, there would be no pharmaceutically active ingredient in the placebo, yet the process of the present invention could be used to make the microballs used as the placebo. The amount of active ingredient can be from about 1 to about 99% of the microballs and the amount of polymer can be from about 99 to about 1% of the microballs. Good results have been obtained with 1 part of active ingredient per 10–30 parts of polymer.

As discussed previously, the amount and the shear rate of stirring are largely dependent on the size of the particles desired. Stirring can commence when the supporting phase is first introduced to the mixing vessel, or stirring can be delayed until the supporting phase has been brought up to the selected temperature. In any case, the stirring must be at a shear rate high enough to form the microballs. The length of stirring at that shear rate will affect the size of the microballs. Stirring of the mixture comprising the supporting phase, the polymer, the active ingredient and any other ingredients at the selected temperature will generally be for a period of time from about 5 minutes to about 2 hours, and more typically from about 10 minutes to about 30 minutes. The size of the particles of the biocompatible polymer used as a starting material is not critical and the size of the particles may be indifferently from about 300 μm to about 5 mm.

The size of the microballs formed will be reduced to the required size according to the amount of stirring and the temperature at which stirring is carried out. For example, particles of 5 mm size may be obtained with relatively low stirring in a high viscosity supporting phase whereas particles of 300 μm size will only be obtained with vigorous stirring in a relatively low viscosity supporting phase. Stirring may be carded out in any conventional manner which gives a shear rate high enough to form microballs, e.g. mechanical stirring, use of an ultra-sound generator or a Polytron mixer from Kinematica GmbH of Luzern, Switzerland. The ultra-sound generator is preferred since it also provides heating.

The "selected temperature" is the temperature to which the mixture is heated to form the microballs. There are a number of limitations on the selected temperature. It must be above the Tg of the selected polymer. However, it cannot be higher than any of the following:

(a) the temperature at which the polymer degrades or vaporizes;

(b) the temperature at which the active ingredient degrades or vaporizes;

(c) the temperature at which the supporting phase degrades or vaporizes.

Obviously, the vaporization temperature will depend on the pressure in the vessel in which the mixture is heated which, in turn, will depend on the polymer employed. As a general rule, a selected temperature which creates no more than about 2 bars of pressure in the reaction vessel is suitable.

The size of the particles produced is a matter of choice and, as previously indicated, is highly dependent on the amount of time and shear rate at which the admixture is stirred at the selected temperature. It is to be noted that the size of the particles affects the burst effect. Larger particles have less burst effect than smaller ones. This means that the burst effect can be controlled by controlling the size of the microballs formed and, in addition, can be controlled by using a mixture of microballs of different diameters.

The present invention also includes the microballs obtained using the process of the present invention. The microballs are characterized by being substantially spherical, having a substantially smooth external surface and having an external surface which is substantially free of active ingredient. The microballs preferably have an average diameter of from about 100 μm to about 5 mm.

The present invention further includes pharmaceutical compositions which contain the microballs of the present invention. The microballs of the present invention may be administered either orally or parenterally. For parenteral administration, it is preferred that the particles have an average diameter which is not greater than about 200 μm. For oral administration, the particles preferably have an average diameter of from about 0.5 to about 5 min.

The invention is illustrated by the following examples:

EXAMPLE 1

The purpose of this example is to demonstrate that there is substantially no active ingredient on the surface of the microballs. The following ingredients were used:

Supporting phase: silicone oil (viscosity, 10,000 mPa.s at 25° C.)

Biocompatible polymer: Poly Lactide co Glycolide (PLGA 50/50, weight average molecular weight range—40,000 to 50,000)

Active ingredient: blue hydrophilic colorant (Blue Patente V)

To a reactor containing 100 ml of silicone oil, there was added 3 g of the mixture of PLGA 50/50. The mixture of PLGA was dispersed for 5 minutes at room temperature under stirring. The stirring was discontinued and the mixture was heated to 110° C. The stirring was resumed and the active ingredient was added. The stirring was maintained for 30 minutes at 125° C. to incorporate the active ingredient. The stirring was stopped and the mixture was allowed to cool overnight in a freezer at 20° C. The mixture was washed with myristic acid isopropyl ester, then filtered and dried to recover blue particles. The length of time and shear rate of the stirring formed particles that had an average diameter of about 10 μm.

Both the silicone oil and the washing agent were studied, and it was found that neither had any blue color. The microballs were then immersed in 200 ml of water and were again studied. Once again, no blue coloration of the water was observed.

The microballs were further treated by diluting them in dichloromethane, which is a solvent for the polymer. This mixture of particles and dichloromethane was then added to water, upon which the water turned blue. This example confirms that there is substantially no active ingredient on the surface of the particles.

EXAMPLE 2

In this example, the following ingredients were used:

Supporting phase: silicone oil (viscosity, 10,000 mPa.s at 25° C.)

Biocompatible polymer: PLGA 50/50, ground to 200 μm

Active ingredient: D-Trp$^6$ LHRH pamoate, particle size 5–10 μm

To a reactor containing 500 ml of silicone oil, there was added 5 g of PLGA 50/50 under stirring. Particles of PLGA 50/50 were dispersed in the oil and the mixture was heated to 80°–100° C. There was then added 0.175 g of particles of peptide while continuing the stirring. The progressive incorporation of the peptide particles in the polymer was observable. The mixture was stirred for 20 minutes at the same temperature and then heated to 125° C. At 125° C. the stirring was stopped. The mixture was cooled to 25° C. It was then diluted with 9 volumes of myristic acid isopropyl ester as washing agent after which it was filtered. The length of time and shear rate of the stirring formed particles that had an average diameter of 5 to 10 μm. The yield was 4.5 g.

EXAMPLE 3

In this example, the following ingredients were used:

Supporting phase: silicone oil (viscosity, 10,000 mPa.s at 25° C.)

Biocompatible polymer: PLGA 50/50, ground to 200 μm

Active ingredient: D-Trp$^6$ LHRH acetate, particle size 5–10 μm

To a reactor containing 500 ml of silicone oil, there was added 5 g of PLGA 50/50 under stirring. Particles of PLGA 50/50 were dispersed in the oil and the mixture was heated to 80°–100° C. There was then added 0.170 g of particles of peptide while continuing the stirring. The progressive incorporation of the peptide particles in the polymer was observable. The mixture was stirred for 20 minutes at the same temperature and then heated to 125° C. At 125° C. the stirring was stopped. The mixture was cooled to 25° C. It was then diluted with 9 volumes of myristic acid isopropyl ester as washing agent after which it was filtered. The length of time and shear rate of the stirring formed particles that had an average diameter of 5 to 10 μm. The yield was 4.8 g.

EXAMPLE 4

In this example, the following ingredients were used:

Supporting phase: silicone oil (viscosity, 10,000 mPa.s at 25° C.)

Biocompatible polymer: PLGA 50/50, ground to 200 μm

Active ingredient: somatulin pamoate

To a reactor containing 500 ml of silicone oil, there was added 5 g of PLGA 50/50 under stirring. Particles of PLGA 50/50 were dispersed in the oil and the mixture was heated to 100°–120° C. There was then added 0.980 g of particles of peptide while continuing the stirring. The progressive incorporation of the peptide particles in the polymer was observable. The mixture was stirred for 30 minutes at the same temperature and then heated to 130° C. At 130° C. the stirring was stopped. The mixture was cooled to 25° C. It was then diluted with 9 volumes of myristic acid isopropyl ester as washing agent after which it was filtered. The length of time and shear rate of the stirring formed particles that had an average diameter of 5 to 10 μm. The yield was 5.1 g.

EXAMPLE 5

In this example, the following ingredients were used:

Supporting phase: Polyvinylpyrrolidone (PvP) K60 in water (45% w/v; viscosity, 10,000 mPa.s at 25° C.)

Biocompatible polymer: PLGA 50/50, ground to 20 μm

Active ingredient: steroids (progesterone), particle size 5–10 μm

To a reactor containing 500 ml of PvP gel, there was added 8 g of PLGA 50/50 under stirring. Particles of PLGA 50/50 were dispersed in the gel and the mixture was heated to 95° C. There was then added 2.44 g of particles of progesterone while continuing the stirring. The progressive incorporation of the peptide particles in the polymer was observable. The mixture was stirred for 30 minutes at 95° C. The stirring was stopped and the mixture was cooled to 25° C. It was then diluted with 10 volumes of water as washing agent after which it was filtered. The length of time and shear rate of the stirring formed particles that had an average diameter of 5 to 10 μm. The yield was 9.96 g.

EXAMPLE 6

In this example, the following ingredients were used:

Supporting phase: silicone oil (viscosity, 10,000 mPa.s at 25° C.)

Biocompatible polymer: ε-caprolactone polymer, ground to 200 μm

Active ingredient: D-Trp$^6$ LHRH pamoate, particle size 5–10 μm

To a reactor containing 500 ml of silicone oil, there was added 1 g of polymer under stirring. Particles of polymer were dispersed in the oil and the mixture was heated to 80° C. There was then added 37 mg of particles of peptide while continuing the stirring. The progressive incorporation of the peptide particles in the polymer was observable. The mixture was stirred for 10 minutes at 110° C. The stirring was stopped and the mixture was cooled to 25° C. It was then diluted with 9 volumes of myristic acid isopropyl ester as washing agent after which it was filtered. The length of time and shear rate of the stirring formed particles that had an average diameter of 5 to 10 μm. The yield was 0.952 g.

EXAMPLE 7

In this example, the following ingredients were used:

Supporting phase: aluminium stearate in sesame oil (4% w/v; viscosity, 12,500 mPa.s at 25° C.)

Biocompatible polymer: PLGA 50/50, ground to 200 μm

Active ingredient: triptoreline pamoate, particle size 5–10 μm

To a reactor containing 500 ml of the supporting phase, there was added 10 g of PLGA 50/50 under stirring. Particles of PLGA 50/50 were dispersed in the gel and the mixture was heated to 120° C. While continuing the stirring there was then added 0.638 g of particles of peptide and 10 mg of sorbitane fatty acid ester. The progressive incorporation of the peptide particles in the polymer was observable. The mixture was stirred for 20 minutes at the same temperature. The stirring was stopped and the mixture was cooled to 25° C. It was then diluted with 20 volumes of ethanol as washing agent after which it was filtered. The length of time and shear rate of the stirring formed particles that had an average diameter of 5 to 10 µm. The yield was 9.2 g.

EXAMPLE 8

In this example, the following ingredients were used:

Supporting phase: aluminium stearate in sesame oil (4% w/v; viscosity, 12,500 mPa.s at 25° C.)

Biocompatible polymer: poly ϵ-caprolactone, ground to 200 µm

Active ingredient: triptoreline pamoate, particle size 5–10 µm

To a reactor containing 500 ml of the supporting phase, there was added 10 g of poly ϵ-caprolactone under stirring. Particles of poly ϵ-caprolactone were dispersed in the gel and the mixture was heated to 120° C. While continuing the stirring there was then added 0.638 g of particles of peptide. The progressive incorporation of the peptide particles in the polymer was observable. The mixture was stirred for 30 minutes at the same temperature. The stirring was stopped and the mixture was cooled to 25° C. It was then diluted with 20 volumes of ethanol as washing agent after which it was filtered. The length of time and shear rate of the stirring formed particles that had an average diameter of 5 to 10 µm. The yield was 8.7 g.

EXAMPLE 9

In this example, the following ingredients were used:

Supporting phase: silicone oil (viscosity, 10,000 mPa.s at 25° C.)

Biocompatible polymer: PLGA 75/25, ground to 200 µm

Active ingredient: tiliquinol (antibacterial), particle size 5–10 µm

To a reactor containing 500 ml of silicone oil, there was added 8 g of PLGA 75/25 and 1.23 g of particles of tiliquinol under stirring. The mixture was heated to 80°–100° C. The progressive formation of the microballs and the incorporation of particles of tiliquinol in said microballs was observable. The mixture was stirred for 30 minutes at the same temperature. The stirring was stopped and the mixture was cooled to 25° C. It was then diluted with 9 volumes of myristic acid isopropyl ester as washing agent after which it was filtered. The length of time and shear rate of the stirring formed particles that had an average diameter of 5 to 10 µm. The yield was 8.25 g.

EXAMPLE 10

In this example, the following ingredients were used:

Supporting phase: aluminium stearate in sesame oil (4% w/v; viscosity, 12,500 mPa.s at 25° C.)

Biocompatible polymer: PLGA 75/25, ground to 200 µm

Active ingredient: tiliquinol (antibacterial), particle size 5–10 µm

To a reactor containing 500 ml of the supporting phase, there was added 2.16 g of particles of the tiliquinol under stirring. Particles of tiliquinol were dispersed in the gel and the mixture was heated to 120° C. While continuing the stirring there was then added 10 g of PLGA 75/25. The progressive formation of the microballs and the incorporation of particles of tiliquinol in said microballs was observable. The mixture was stirred for 25 minutes at the same temperature. The stirring was stopped and the mixture was cooled to 25° C. It was then diluted with 20 volumes of ethanol as washing agent after which it was filtered. The length of time and shear rate of the stirring formed particles that had an average diameter of 5 to 10 µm. The yield was 11.3 g.

It will be understood that the claims are intended to cover all changes and modifications of the preferred embodiments of the invention herein chosen for the purpose of illustration which do not constitute a departure from the spirit and scope of the invention.

What is claimed is:

1. A method of preparing microballs, said method comprising the steps of:
    (a) stirring a mixture of a biocompatible polymer and an active ingredient in a solvent free liquid polymeric supporting phase, said biocompatible polymer and said active ingredient being separate components, said mixtures being stirred at a selected temperature above the glass transistion temperature of the bicompatible polymer and below the temperature at which any one of the active ingredient, bicompatible polymer, and polymeric supporting phase degrades or vaporizes, said bicompatible polymer and said active ingredient being immiscible in said polymeric supporting phase;
    (b) continuing stirring for a period of time and at a shear rate that produces microballs of a desired average diameter;
    (c) cooling the mixture including the microballs, and
    (d) separate the microballs from the polymeric supporting phase.

2. The method of claim 1 wherein the active ingredient is added to the polymeric supporting phase before the supporting phase is heated.

3. The method of claim 1 wherein the biocompatible polymer is added to the polymeric supporting phase before the polymeric supporting phase is heated.

4. The method of claim 1 wherein both the active ingredient and the biocompatible polymer are added to the polymeric supporting phase before the polymeric supporting phase is heated.

5. The method of claim 4 wherein the active ingredient and biocompatible polymer are pre-mixed before they are added to the polymeric supporting phase.

6. The method of claim 1 wherein the active ingredient is added to the polymeric supporting phase after the supporting phase is heated.

7. The method of claim 1 wherein the bicompatible polymer is added to the supporting phase after the supporting phase is heated.

8. The method of claim 1 wherein both the active ingredient and the biocompatible polymer are added to the polymeric supporting phase after the polymeric phase is heated.

9. The method of claim 1 wherein the biocompatible polymer is added to the polymeric supporting phase; the biocompatible polymer and the polymeric supporting phase are heated and stirred to form microballs; and thereafter the active ingredient is added and incorporated into the microballs with additional stirring.

10. The method of claim 8 wherein the active ingredient and bicompatible polymer are pre-mixed before they are added to the polymeric supporting phase.

11. The method of claim 1 wherein the selected temperature creates less than about 2 bars of pressure in the reaction vessel.

12. The method of claim 1 wherein the stirring at the selected temperature is for a period of from about 5 minutes to about 2 hours.

13. The method of claim 1 wherein the stirring at the selected temperature is for a period of from about 10 minutes to about 30 minutes.

14. The method of claim 1 wherein the polymeric supporting phase has a viscosity of from about 3,000 to about 15,000 mPa.s at 25° C.

15. The method of claim 1 wherein the polymeric supporting phase has a viscosity of from about 5,000 to about 12,000 mPa.s at 25° C.

16. The method of claim 1 wherein the polymeric supporting phase has a viscosity which is about 10,000 mPa.s at 25° C.

17. The method of claim 1 wherein the polymeric supporting phase is a hydrophobic gel.

18. The method of claim 17 wherein the hydrophobic gel is a thickened oil.

19. The method of claim 1 wherein the polymeric supporting phase is a hydrophilic gel.

20. The method of claim 19 wherein the hydrophilic gel is an aqueous gel.

21. The method of claim 1 wherein the polymeric supporting phase is selected from the group consisting of silicone oil, sesame oil, peanut oil and castor oil.

22. The method of claim 1 wherein the biocompatible polymer is biodegradable.

23. The method of claim 1 wherein the biocompatible polymer is bioresorbable.

24. The method of claim 1 wherein the biocompatible polymer has a glass transition temperature between about 25° C. and about 200° C.

25. The method of claim 1 wherein the biocompatible polymer has a glass transition temperature between about 35° C. and about 150° C.

26. The method of claim 1 wherein the biocompatible polymer is a copolymer of lactic acid and glycolic acid.

27. The method of claim 26 wherein the lactic acid and glycolic acid are present in a ratio of 50:50.

28. The method of claim 1 wherein the active ingredient is a peptide.

29. The method of claim 28 wherein the active ingredient is an ester of D-Trp$^6$ LHRH.

30. The method of claim 1 wherein the active ingredient is present in an amount of from about 1% to about 99% and the biocompatible polymer is present in an amount of from about 99% to about 1%.

31. The method of claim 1 wherein the active ingredient is present in an amount of one part of active ingredient to 10–30 parts of biocompatible polymer.

32. The method of claim 1 wherein stirring is continued until the microballs have an average diameter of from about 0.5 mm to about 5 mm.

33. The method of claim 1 wherein stirring is continued until the microballs have an average diameter which is not greater than about 200 μm.

34. The method of claim 1 wherein the mixture further comprises pharmaceutically inert additives.

35. The method of claim 1 wherein the active ingredient is in solid form.

36. The method of claim 1 wherein the active ingredient is in liquid form.

37. A method of preparing uncoated microballs, said method comprising the steps of:

(a) stirring a mixture of a biocompatible polymer and an active ingredient in a solvent free liquid polymeric supporting phase, said biocompatible polymer and said active ingredient being separate components, said mixture being stirred at a selected temperature above the glass transition temperature of the bicompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear rate that produces microballs of a desired average diameter;

(c) cooling the mixture including the uncoated microballs; and (d) separating the uncoated microballs from the polymeric supporting phase.

38. A method of preparing microballs, said method consisting essentially of the steps of:

(a) stirring a mixture of a biocompatible polymer and an active ingredient in a solvent-free liquid polymeric supporting phase, said bicompatible polymer and said active ingredient being separate components, said mixture being stirred at a selected temperature above the glass transition temperature of the biocompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear that produces microballs of a desired average diameter;

(c) cooling the mixture including the uncoated microballs; and (d) separating the microballs from the polymeric supporting phase.

39. A method of preparing microballs, said method comprising the steps of:

(a) stirring a mixture of a biocompatible polymer and an active ingredient in a solvent-free liquid polymeric supporting phase, said biocompatible polymer and said active ingredient being separate components, said mixture being stirred at a selected temperature above the glass transition temperature of the biocompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear rate that produces microballs of a desired average diameter;

(c) cooling the mixture including the microballs; and (d) separating the microballs from the polymeric supporting phase.

40. A method of preparing uncoated microballs, said method consisting essentially of the steps of:

(a) stirring a mixture of a biocompatible polymer and an active ingredient in a liquid polymeric supporting phase, said biocompatible polymer and said active ingredient being separate components, said mixture being stirred at a selected temperature above the glass transition temperature of the biocompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear rate that produces uncoated microballs of a desired average diameter;

(c) cooling the mixture including the uncoated microballs; and (d) separating the uncoated microballs from the polymeric supporting phase.

41. A method of preparing uncoated microballs, said method comprising the steps of:

(a) stirring a mixture of a biocompatible polymer and an active ingredient in a solvent-free liquid polymeric supporting phase, said biocompatible polymer and said active ingredient being separate components, said mixture being stirred at a selected temperature above the glass transition temperature of the biocompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear rate that produces uncoated microballs of a desired average diameter;

(c) cooling the mixture including the uncoated microballs; and (d) separating the uncoated microballs from the polymeric supporting phase.

42. A method of preparing microballs, said method consisting essentially of the steps of:

(a) stirring a mixture of a biocompatible polymer and an active ingredient in a solvent-free liquid polymeric supporting phase, said biocompatible polymer and said active ingredient being separate components, said mixture being stirred at a selected temperature above the glass transition temperature of the biocompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear rate that produces microballs of a desired average diameter;

(c) cooling the mixture including the microballs; and (d) separating the microballs from the polymeric supporting phase.

43. A method of preparing uncoated microballs, said method consisting essentially of the steps of:

(a) stirring a mixture of a biocompatible polymer and an active ingredient in a solvent-free liquid polymeric supporting phase, said biocompatible polymer and said active ingredient being separate components, said mixture being stirred at a selected temperature above the glass transition temperature of the biocompatible polymer and below the temperature at which any one of the active ingredient, biocompatible polymer, and polymeric supporting phase degrades or vaporizes, said biocompatible polymer and said active ingredient being immiscible in said polymeric supporting phase;

(b) continuing stirring for a period of time and at a shear rate that produces uncoated microballs of a desired average diameter;

(c) cooling the mixture including the uncoated microballs; and (d) separating the uncoated microballs from the polymeric supporting phase.

* * * * *

UNITED STATES PATENT AND TRADEMARK OFFICE
CERTIFICATE OF CORRECTION

PATENT NO. : 5,569,467
DATED : October 29, 1996
INVENTOR(S) : Jean-Marc Ruiz

Page 1 of 2

It is certified that error appears in the above-indentified patent and that said Letters Patent is hereby corrected as shown below:

Column 2, line 23, after "material" insert --occurs--.

Column 3, line 59, after "polymer" insert --is heated--.

Column 4, line 26, change "Silicon" to --Silicone--; line 30, change "silicon" to --silicone--.

Column 5, line 62, change "carded" to --carried--.

Column 6, line 41, change "min" to --mm--.

Column 7, line 34, after "as" insert --a--.

Column 8, line 20, change "20" to --200--.

Column 10 (claim 1), line 27, change "bicompatible" to --biocompatible--; line 29, change "bicompatible" to --biocompatible--; lines 30-31, change "bicompatible" to --biocompatible--; line 37, change "separate" to --separating--.

Column 10 (claim 2), line 40, after "the" (second instance), insert --polymeric--.

Column 10 (claim 6), line 53, after "the" (second instance), insert --polymeric--.

Column 10 (claim 7), line 55, change "bicompatible" to --biocompatible--; line 56, after "the" (both instances), insert --polymeric--.

Column 10 (claim 8), line 60, after "polymeric" (second instance), insert --supporting--.

UNITED STATES PATENT AND TRADEMARK OFFICE
CERTIFICATE OF CORRECTION

PATENT NO. : 5,569,467
DATED : October 29, 1996
INVENTOR(S) : Jean-Marc Ruiz

It is certified that error appears in the above-indentified patent and that said Letters Patent is hereby corrected as shown below:

Column 11 (claim 10), line 2, change "bicompatible" to --biocompatible--.

Column 12 (claim 37), line 6, delete "solvent free"; line 10, change "bicompatible" to --biocompatible--.

Column 12 (claim 38), line 26, delete "solvent-free"; line 27, change "bicompatible" to --biocompatible--; line 39, delete "uncoated".

Signed and Sealed this

Twenty-eighth Day of January, 1997

Attest:

BRUCE LEHMAN

Attesting Officer     Commissioner of Patents and Trademarks